United States Patent [19]
Conley et al.

[11] Patent Number: 6,051,255
[45] Date of Patent: *Apr. 18, 2000

[54] POLYMER COATED TABLET COMPRISING AMOXYCILLIN AND CLAVULANATE

[75] Inventors: Creighton Pierce Conley; Nigel Philip McCreath Davidson, both of Bristol, Tenn.; Ernest Lionel Gilbert Rivett, Arundel; Kenneth Trevor Yeates, Grays, both of United Kingdom

[73] Assignee: SmithKline Beecham plc, Brentford, United Kingdom

[*] Notice: This patent issued on a continued prosecution application filed under 37 CFR 1.53(d), and is subject to the twenty year patent term provisions of 35 U.S.C. 154(a)(2).

[21] Appl. No.: 08/727,581
[22] PCT Filed: Apr. 19, 1995
[86] PCT No.: PCT/EP95/01463
§ 371 Date: Dec. 19, 1996
§ 102(e) Date: Dec. 19, 1996
[87] PCT Pub. No.: WO95/28927
PCT Pub. Date: Nov. 2, 1995

[30] Foreign Application Priority Data
Apr. 23, 1994 [GB] United Kingdom ................... 9408117

[51] Int. Cl.[7] .............................. A61K 9/30; A61K 9/32; A61K 9/36
[52] U.S. Cl. ......................... 424/482; 424/465; 424/474; 424/475; 424/480; 514/770; 514/772.3; 514/778; 514/781
[58] Field of Search ...................................... 424/465, 480, 424/482, 464, 474, 475, 479

[56] References Cited

U.S. PATENT DOCUMENTS

| | | | |
|---|---|---|---|
| 4,232,005 | 11/1980 | Howarth | 424/114 |
| 4,441,609 | 4/1984 | Crowley | 206/204 |
| 4,537,887 | 8/1985 | Rooke et al. | 514/197 |

FOREIGN PATENT DOCUMENTS

| | | |
|---|---|---|
| 0 049 061 | 7/1982 | European Pat. Off. ......... A61K 9/20 |
| 0080862 | 6/1983 | European Pat. Off. . |

OTHER PUBLICATIONS

Repertoria Farmaceutico Italiano (1989) pp. A105–A108 and English Translation.
Pharmaceutical Dosage Forms, vol. 3, (1990), pp. 93–97.
Drug Development and Industrial Pharmacy, 3(3), 227–240 (1977).
Repertoria Farmaceutico Italiano(1992) pp. A–75.
Repertoria Farmaceutico Italiano (1993) pp. A79–80.
Repertoria Farmaceutico Italiano (1994) pp. A72.

*Primary Examiner*—James M. Spear
*Attorney, Agent, or Firm*—Dara L. Dinner; Stephen Venetianer; Charles M. Kinzig

[57] ABSTRACT

The present invention is to a tablet formulation, being a medicament for oral administration for the treatment of bacterial infections, the tablet comprising a compacted mixture of 750–950 mg of amoxycillin and a quantity of clavulanate in a weight ratio of amoxycillin:clavulanate between 6:1 to 8:1 inclusive, and having a film coating of polymers which can be applied by aqueous film coating techniques.

27 Claims, No Drawings

POLYMER COATED TABLET COMPRISING AMOXYCILLIN AND CLAVULANATE

This application is a 371 of PCT/EP95/01463 filed Apr. 19, 1995.

The present invention relates to medicaments for oral administration in the treatment of bacterial infections, comprising amoxycillin and salts of clavulanic acid.

Amoxycillin and its derivatives, e.g. amoxycillin trihydrate, are known (e.g. GB 1241844) as antibacterial agents useful in the treatment of gram-negative and gram-positive bacterial infections. Clavulanic acid and its derivatives, e.g. its salts such as potassium clavulanate, are known (e.g. GB 1508977) as β-lactamase inhibitors which inhibit the activity of β-lactamase enzymes produced by bacteria and which confer antibiotic resistance by destroying β-lactam antibiotics such as amoxycillin. The terms "amoxycillin" and "clavulanate" used herein unless otherwise specified include both the free parent acids and derivatives such as salts thereof. The use of clavulanate in combination with amoxycillin consequently enhances the effectiveness of amoxycillin.

The use of potassium clavulanate in combination with amoxycillin trihydrate within the ratios amoxycillin:clavulanic acid 1:1 to 6:1, (expressed in terms of the weight of parent compound amoxycillin or clavulanic acid, this terminology being used throughout this description unless otherwise stated) is described in GB 2005538. Potassium clavulanate is an exceptionally difficult material to formulate, being extremely hygroscopic and moisture sensitive. Degradation readily occurs in the presence of water and aqueous media.

Known formulations of amoxycillin and clavulanate are provided for administration three times daily (i.e. "tid" dosing). It is desirable for inter alia patient convenience and compliance that such formulations be provided for administration twice daily (i.e. "bid" dosing). It is also highly desirable that such formulations should have a consistent bioavailability of the active ingredients clavulanate and amoxycillin.

An amoxycillin/clavulanate formulation has been produced which enables bid dosage, and also has the unexpected benefit of a particularly consistent bioavailability, particularly of clavulanate. In some instances the formulation may also show a increased bioavailability.

Accordingly the present invention provides a tablet formulation, being a medicament for oral administration for the treatment of bacterial infections, the tablet comprising a compacted mixture of 750–950 mg of amoxycillin and a quantity of clavulanate, in a weight ratio amoxycillin:clavulanate between 6:1 to 8:1 inclusive, and having a film coating of polymers which can be applied by aqueous film coating techniques.

Suitable derivatives of amoxycillin are amoxycillin trihydrate, anhydrous amoxycillin and alkali metal salts of amoxycillin such as sodium amoxycillin. Suitable derivatives of clavulanic acid are alkali metal salts of clavulanic acid such as potassium clavulanate. It is preferred to use amoxycillin trihydrate and potassium clavulanate in combination in a tablet formulation of this invention containing the two, this combination having met with regulatory approval, and being particularly advantageous.

Suitably the tablet contains nominally 875 mg of amoxycillin ±10% and 125 mg of clavulanate ±10%, i.e. in a ratio amoxycillin:clavulanate of nominally 7:1. The tablet of the invention may suitably contain 50 wt. % or more, for example around 65–75 wt. % of the combination of amoxycillin and clavulanate, e.g. typically 70 wt. % +2 wt %.

The tablet formulation of this invention may be provided for treatment of bacterial infections generally, for example one or more of inter alia upper respiratory tract infections, lower respiratory tract infections, genito-urinary tract infections and skin and soft tissue infections. The tablet formulation of this invention is generally suitable for treatment of infections by microorganisms which are susceptible to β-lactam antibiotics, and may also have efficacy for some penicillin-resistant microorganisms.

The tablet formulation of the invention may include one or more other additional excipients etc. generally conventional to the dosage form in question. For example tablet dosage forms may contain one or more conventional diluents such as microcrystalline cellulose (which can also function as a compression aid) e.g. comprising around 20–35 wt % of the tablet e.g. 25–30 wt %; disintegrants such as sodium starch glycolate, e.g. comprising 0.5–3.5 wt % of the tablet e.g. 1.75–2.25 wt %; lubricants such as magnesium stearate e.g. comprising 0.5–1.5 wt % of the tablet e.g. 0.75–1.25 wt % and glidants, such as colloidal silicon dioxide, e.g. comprising 0.25–1.0 wt % of the tablet e.g. 0.5–0.9 wt %. Although the above-listed classes and examples of excipients, together with the active ingredients may make up the 100% uncoated core weight of the tablet, in addition the tablet forms may contain flavouring agents, colourants, preservatives, desiccants etc. conventional to the dosage form in question up to the 100% uncoated core weight of the tablet.

Tablets of the invention may be made by conventional tablet manufacturing techniques, e.g. blending of the ingredients followed by dry compaction, granulation then compaction of the granulate to form the compacted tablet core. A suitable granulate may be produced for example by slugging or roller compaction.

Roller compaction generally involves a screening procedure that can lead to a narrower particle size distribution with fewer particles at either extreme of the size range. Roller compaction may also be better suited to large scale and continuous of the granulate from which the tablet of the invention is formed, because although pharmaceutically slugging and roller compaction are generally considered as entirely equivalent, in the tablet of the invention roller compaction is found to contribute to an unexpected increase in consistency of bioavailability and is hence preferred. A suitable method of roller compaction is via use of the known "Chilsonator" roller compactor. A description of such a roller compactor is included in for example "The Theory and Practice of Industrial Pharmacy" Lachan et al. 3rd Edn. Lea & Febiger (1986) page 318–320. It is also preferred that the preparation of the formulations of the invention is carried out under conditions of low humidity, e.g. less than 30% RH, more suitably less than 20% RH, ideally as low as possible, to assist in preservation of the highly moisture sensitive clavulanate, particularly potassium clavulanate.

Polymers which can be applied by aqueous film coating may facilitate application of the film coating by aqueous film coating techniques, thereby avoiding the need for organic solvents. Suitable polymers include hydroxypropylcellulose, hydroxypropylmethyl cellulose, ethylcellulose (for example ethylcellulose in a latex composition as supplied by the FMC Corporation as "AquaCoat" (trade mark)), methylhydroxyethylcellulose, polyvinylpyrrolidone ("PVP", e.g. as supplied under the name Povidone (trade mark), sodium carboxymethylcellulose and acrylate polymers (e.g. the known methacrylic acid esters supplied under the trade name "Eudragit" (trade mark)).

A preferred polymer is hydroxypropylmethylcellulose ("HPMC") suitably ill combination with a polyethylene glycol ("PEG"). PEG's of low molecular weight (200 to 600 series) are liquid at room temperature and find use as plasticisers. PEG's with high molecular weights (900 to 8000) are waxy solids at room temperature and are used in combination with low molecular weight PEG's and with other polymers such as HPMC to modify film properties and to contribute to tablet sheen.

A preferred polymer which can be applied by aqueous film coating techniques is one or more hydroxypropylmethyl celluloses combined with one or more PEG's. HPMC polymers have the advantages of solubility in physiological fluids as well as water, non-interference with tablet disintegration, dissolubility or drug availability, formation of a flexible film, freedom from objectionable taste or odour, stability to heat, light, air, moisture, compatibility to stabilisers, colourants opacifiers, and gloss. The hydroxypropylmethylcellulose functions as a film former, and the polyethylene glycol functions as a plasticiser. The hydroxypropylmethyl cellulose:polyethylene glycol ratio in the film coating is suitably between 7.5:1 to 5.5:1, e.g. around 6.5:1±10%. Suitably the hydroxypropylmethyl cellulose is applied in the form of a mixture of hydroxypropylmethyl cellulose 6 cps and 15 cps, in a ratio of around 2:1 to 4:1 e.g. around 3:1±10%. Suitably the polyethylene glycol is applied in the form of a mixture of polyethylene glycol 4000* and 6000* in a ratio between around 1:2 to 2:1, e.g. around 1:1 (* in the USA these materials are supplied as polyethylene glycol 3350 and 6000* respectively). The film coat may also suitably include an opacifier, for example titanium dioxide (white). Suitably the opacifier may be present in around a 1:1±10% proportion with the hydroxypropylmethyl cellulose in the film coat.

The materials of the film coat are preferably applied by an aqueous film coating process, as application in this way form a film of a nature which also appears to contribute to the improved consistency in bioavailability. A suitable solids loading for the aqueous film coat is around 10–30% w/v, typically 10–20%, e.g. 15%±2%.

Suitably the film coating is applied so as to deposit a weight of dried film materials corresponding to around 1.0–4.0 wt. % of the total coated tablet weight.

Preferably the dosage forms of the medicament of the invention are packaged in a container that inhibits the ingress of atmospheric moisture, e.g. blister packs or tightly closeable bottles etc. as conventional in the art. Preferably bottles also include a desiccant material to preserve the clavulanate.

The unit dosage form(s) of the medicament of the invention may suitably be for oral administration, for example at intervals separated by 6 or more hours, e.g. separated by 8 or more hours, e.g. separated by up to around 12 hours. Although particularly suited to bid dosing, the tablet formulation of this invention may also be administered at a greater frequency e.g. tid dosing, for appropriate indications and within approved dosing limits.

Suitable total daily dosages of amoxycillin are in the range 900–1800 mg daily, preferably 1000–1750 mg inclusive daily. Suitable total daily dosages of clavulanic acid are in the range 200–300 mg daily, preferably 250±10 mg inclusive daily. Within the total daily dosages referred to above, for oral administration bid, the tablet of the invention may be orally administered at intervals separated by around 8–12 hours.

The invention further provides a method of treatment of bacterial infections in human beings or in animals comprising the oral administration to a human being or animal in need of such treatment of a medicament as described above not more than twice a day.

The invention also provides a method for the preparation of a tablet formulation, being a medicament for oral administration for the treatment of bacterial infections, which comprises compacting a mixture of 750–950 mg of amoxycillin and a quantity of clavulanate, in a weight ratio amoxycillin:clavulanate between 6:1 and 8:1 inclusive, and coating the compact with a film coating which comprises hydroxypropylmethyl celluloses and polyethylene glycols.

Suitable and preferred forms of this process are as described above with reference to the tablet formulation itself *mutates muianis*.

The invention also provides a tablet formulation as described above for use as an active therapeutic substance.

The invention also provides a tablet formulation as described above for use in the treatment of bacterial infections.

The invention also provides the use of a tablet formulation as described above in the manufacture of medicament for use in the treatment of bacterial infections.

The invention also provides a method of treating a bacterial infection in a human patient which includes the step of administering an effective amount of amoxycillin and clavulanate comprised in a tablet formulation as described above.

The invention will now be described by way of example only.

EXAMPLE 1.

A tablet formulation was prepared having the following composition:

| Ingredient | (mg.) | wt. % | Function | Ref. to Std. |
|---|---|---|---|---|
| Active Constituents[1]: | | | | |
| Amoxycillin trihydrate (equivalent to amoxycillin) | 1017.4 875.00 | 70.2 | Active ingdt. | EP |
| Potassium clavulanate (equivalent to clavulanic acid) | 152.45 125.0 | 10.5 | Active ingdt. | G319 |
| Other Constituents: | | | | |
| Magnesium Stearate | 14.50 | 1.00 | Lubricant | NF |
| Sodium Starch Glycollate | 29.00 | 2.00 | Disintegrant | NF |
| Colloidal Silicon Dioxide | 10.0 | 0.70 | Glidant | NF |
| Microcrystalline Cellulose | 226.65 | 15.6 | Compression aid & Diluent | NF |
| Core tablet weight | 1450.00 | 100.00 | | |
| Film Coat[2] | | | | |
| Purified Water | NA | NA | Solvent | USP |
| Opadry White YS-1-7700 | 32.0 | 2.2 | Film Coat | NA |
| Opadry White YS-1-7700 can be broken down as below: | | | | |
| Titanium Dioxide | 13.76 | 43.0 | Opacifier | EP |
| Hydroxypropylmethyl cellulose 6 cps | 10.56 | 33.0 | Film Former | |
| Hydroxypropylmethyl cellulose 15 cps | 3.52 | 11.0 | Film Former | JP |
| Polyethylene Glycol 3350[3] | 2.08 | 6.5 | Plasticizer | USNF |
| Polyethylene Glycol 8000[3] | 2.08 | 6.5 | Plasticizer | USNF XVII |

-continued

A tablet formulation was prepared having the following composition:

| Ingredient | (mg.) | wt. % | Function | Ref. to Std. |
|---|---|---|---|---|
| Purified Water[4] | NA | NA | Solvent[4] | USP |
| Nominal coated tablet weight: | 1482.00 | | | |

[1]These amounts are dependent upon the potencies of the actives used and are based on 86% for amoxycillin and 82% for potassium clavulanate (clavulanate potassium 41% is part of a 1:1 blend with microcrystalline cellulose). Constant tablet weight is maintained through adjustment of the quantity of microcrystalline cellulose according to the potency of the actives.
[2]The Film coat constituents may be supplied as a dry powder blender either, ex Colorcon, as Opadry White YS-1-7700 in the USA or Opadry white OY-S-7300 in Europe. Wt. % for film coat constituents are expressed as a percentage of the Opadry film weight.
[3]Polyethylene Glycols 3350 and 8000 are supplied in Europe as Polyethylene Glycols 4000 and 6000 respectively.
[4]The Purified Water is removed during processing.

The Film Coat is applied to 100% of the core weight.

The tablets were made by blending the amoxycillin, potassium clavulanate, and portions of microcrystalline cellulose and magnesium stearate, roller compacting (chilsonating) this blend, then blending with the other constituents, before tabletting on a conventional tablet press and coating. The process is described in more detail below.

All components are sifted or charged to the blender through a vibratory feeder equipped with a 4 mesh screen or through a 14 mesh blender screen, and through a mill unless otherwise noted. The mill is operated at 1500 rpm, knives forward, with a 0.093 inch perforated plate.

An approximately ⅔ portion of the microcrystalline cellulose is loaded into a suitable blender. An approximately ⅕ portion of the amoxycillin trihydrate is loaded into the blender. Half of the magnesium stearate is loaded through a 14 mesh screen into the blender. The mix is blended for two minutes. Another ⅖ portion of amoxycillin trihydrate and ½ of the potassium clavulanate/microcrystalline cellulose blend is loaded into the blender. The mix is blended for three minutes The remainder of the amoxycillin trihydrate and of the potassium clavulanate/microcrystalline cellulose blend is then loaded into the blender. The mix is blended for five minutes.

The blended contents are passed through a Chilsonator of appropriate capacity, under a pressure of 1000 psi, then discharged through a Fitzmill operating at 1800 rpm, knives forward, with a 0.079"–0.109" perforated plate, followed by screening over a vibrascreen fitted with an upper screen of 14 mesh and a lower screen of 18 mesh, recycling and recompacting the over- and under-sized granulation until the acceptable sieve cut is 98% of the load.

Approximately a 10% portion of the granulation is loaded into the blender, bypassing the mill. The colloidal silicon dioxide, sodium starch glycollate and remaining portions of magnesium stearate and microcrystaline cellulose are loaded into the blender, and the mix is blended for five minutes. The remaining granulation is loaded into the mixer, by-passing the mill, and blended for 15 minutes.

The blend is compressed, using a suitable tablet press fitted with 0.3937"×0.8465" capsule shaped punches, to form tablets having a weight of 1.450 g with hardness and thickness values within manufacturing guidelines for pharmaceutical tablets.

The tablet cores are then coated with the aqueous film coat at a 300 Kg batch size in a 60" (150 cm) coating pan. The preferred coating process requires dehumidified inlet air at a sufficient temperature that can produce a relative exhaust humidity of less than 12% during the spraying operation.

In a clinical trial the tablet of Example 1 showed a decreased inter subject variability. Although specifically exemplified by the tablet of Example 1, this effect may also be observed with pharmaceutically equivalent tablets having a composition in which the proportions of ingredients differ within for example +10%, e.g. +5% of the values given in Example 1.

What is claimed is:

1. A process for preparing a tablet formulation containing a tablet core which process comprises:

a) compacting a mixture of amoxycillin and clavulanate;

b) coating the compact mixture in part (a) with a film coating of polymers applied by aqueous film coating techniques.

2. A process according to claim 1 which further comprises the preliminary steps of preparing granulates which comprise a mixture of amoxycillin and clavulanate by roller compaction; and, thereafter, compacting the granulates along with excipients into tablet cores.

3. A process for preparing a tablet formulation which comprises compacting a mixture of 750–950 mg of amoxycillin and a quantity of clavulanate, in a weight ratio amoxycillin:clavulanate between 6:1 and 8:1 inclusive, and coating the compacted mixture with a film coating which comprises hydroxypropylmethyl cellulose and polyethylene glycol; and wherein the polyethylene glycol is applied in the form of a mixture of polyethylene glycol 4000 and 6000 in a ratio between 1:2 to 2:1.

4. The process according to claim 3 wherein the film coating is applied by aqueous film coating techniques.

5. The process according to claim 1 wherein the amoxycillin is in the form of amoxycillin trihydrate and the clavulanate is in the form of potassium clavulanate.

6. The process according to claim 1 wherein the tablet contains 875 mg of amoxycillin ±10% and 125 mg of clavulanate ±10%, such that the ratio of amoxycillin:clavulanate is 7:1.

7. The process according to claim 1 wherein the tablet additionally contains microcrystalline cellulose comprising 20–35 wt % of the tablet; sodium starch glycolate comprising 0.5–3.5 wt % of the tablet; magnesium stearate comprising 0.5–1.5 wt % of the tablet; colloidal silicon dioxide comprising 0.25–1.0 wt % of the tablet; together with the active ingredients making up the 100% uncoated core weight of the tablet.

8. The process according to claim 1 wherein the film coating comprises hydroxypropylcellulose, hydroxypropylmethyl cellulose, ethylcellulose, methylhydroxyethylcellulose, polyvinylpyrrolidone, sodium carboxymethylcellulose or acrylate polymers.

9. The process according to claim 8 wherein the film coating polymers comprises hydroxypropylmethylcellulose in combination with a polyethylene glycol.

10. The process according to claim 9 wherein the hydroxypropylmethyl cellulose:polyethylene glycol ratio in the film coating is between 7.5:1 to 5.5:1.

11. The process according to claim 9 wherein the polyethylene glycol is applied in the form of a mixture of polyethylene glycol 4000 and 6000 in a ratio between 1:2 to 2:1.

12. The process according to claim 1 wherein the weight of dried film coating polymers corresponds to around 1.0–4.0 wt. % of the total coated tablet weight.

13. The process according to claim 1 wherein the compacted mixture of step (a) contains 750–950 mg of amoxycillin and a quantity of clavulanate in a weight ratio amoxycillin:clavulanate between 6:1 to 8:1 inclusive.

14. The product produced by the process according to claim 1.

15. A tablet formulation comprising a compacted mixture of amoxycillin and clavulanate and having a film coating of polymers which is applied by aqueous film coating techniques which further comprises microcrystalline cellulose comprising 20–35 wt % of the tablet; sodium starch glycolate comprising 0.5–3.5 wt % of the tablet; magnesium stearate comprising 0.5–1.5 wt % of the tablet; colloidal silicon dioxide comprising 0.25–1.0 wt % of the tablet; together with the active ingredients making up the 100% uncoated core weight of the tablet.

16. A tablet formulation according to claim 15 in which the film coating comprises hydroxypropylmethylcellulose in combination with a polyethylene glycol.

17. A tablet formulation according to claim 16 in which the hydroxypropylmethyl cellulose:polyethylene glycol ratio in the film coating is between 7.5:1 to 5.5:1.

18. A tablet formulation according to claim 16 in which the polyethylene glycol is applied in the form of a mixture of polyethylene glycol 4000 and 6000 in a ratio between 1:2 to 2:1.

19. A tablet formulation according to claim 15 in which the weight of dried film coating materials corresponds to around 1.0–4.0 wt. % of the total coated tablet weight.

20. A tablet formulation according to 15 in which the amoxycillin is in the form of amoxycillin trihydrate and the clavulanate is in the form of potassium clavulanate.

21. A tablet formulation according to claim 15 in which the tablet contains 875 mg of amoxycillin ±10% and 125 mg of clavulanate ±10%, such that the ratio of amoxycillin:clavulanate is 7:1.

22. A tablet formulation comprising a compacted mixture of amoxycillin and clavulanate and having a film coating of polymers which are hydroxypropylmethyl-cellulose in combination with a polyethylene glycol, and which coating of polymers is applied by aqueous film coating techniques.

23. A tablet formulation according to claim 22 in which the hydroxypropylmethyl cellulose:polyethylene glycol ratio in the film coating is between 7.5:1 to 5.5:1.

24. A tablet formulation according to claim 23 in which the polyethylene glycol is applied in the form of a mixture of polyethylene glycol 4000 and 6000 in a ratio between 1:2 to 2:1.

25. A tablet formulation according to claim 22 in which the weight of dried film coating materials corresponds to around 1.0–4.0 wt. % of the total coated tablet weight.

26. A tablet formulation according to claim 22 in which the amoxycillin is in the form of amoxycillin trihydrate and the clavulanate is in the form of potassium clavulanate.

27. A tablet formulation according to claim 22 in which the tablet contains 875 mg of amoxycillin ±10% and 125 mg of clavulanate ±10%, such that the ratio of amoxycillin:clavulanate is 7:1.

* * * * *